US008571892B2

(12) United States Patent
Averill et al.

(10) Patent No.: US 8,571,892 B2
(45) Date of Patent: *Oct. 29, 2013

(54) METHOD OF GROUPING AND ANALYZING CLINICAL RISKS

(75) Inventors: Richard Francis Averill, Seymour, CT (US); Jon Eisenhandler, Bristol, CT (US); Norbert Israel Goldfield, Northampton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 1883 days.

This patent is subject to a terminal disclaimer.

(21) Appl. No.: 11/465,901

(22) Filed: Aug. 21, 2006

(65) Prior Publication Data

US 2006/0287888 A1 Dec. 21, 2006

Related U.S. Application Data

(62) Division of application No. 09/302,336, filed on Apr. 29, 1999, now Pat. No. 7,127,407.

(51) Int. Cl.
*G06Q 10/00* (2012.01)
*G06Q 50/00* (2012.01)
*G06Q 40/00* (2012.01)

(52) U.S. Cl.
USPC ........................................ 705/3; 705/2; 705/4

(58) Field of Classification Search
USPC ....................................................... 705/2, 3
See application file for complete search history.

(56) References Cited

U.S. PATENT DOCUMENTS

| 5,018,067 | A | | 5/1991 | Mohlenbrock et al. | |
|---|---|---|---|---|---|
| 5,229,584 | A | | 7/1993 | Erickson | |
| 5,253,164 | A | | 10/1993 | Holloway et al. | |
| 5,301,105 | A | * | 4/1994 | Cummings, Jr. | 705/2 |
| 5,307,262 | A | * | 4/1994 | Ertel | 705/2 |
| 5,483,443 | A | * | 1/1996 | Milstein et al. | 705/3 |
| 5,486,999 | A | | 1/1996 | Mebane | |
| 5,493,492 | A | * | 2/1996 | Cramer et al. | 705/32 |
| 5,508,912 | A | | 4/1996 | Schneiderman | |
| 5,557,514 | A | | 9/1996 | Seare et al. | |
| 5,809,476 | A | * | 9/1998 | Ryan | 705/2 |
| 5,835,897 | A | | 11/1998 | Dang | |
| 5,956,689 | A | * | 9/1999 | Everhart, III | 705/3 |
| 6,112,182 | A | * | 8/2000 | Akers et al. | 705/2 |
| 6,370,511 | B1 | | 4/2002 | Dang | |

FOREIGN PATENT DOCUMENTS

| WO | 9117510 | 11/1991 |
|---|---|---|
| WO | 9701141 | 1/1997 |

OTHER PUBLICATIONS

'Doctors need to practice better billing management', Westchester County Business Journal, Apr. 29, 1996, vol. 35 Issue 18, p. 27. 1/4 p.*

(Continued)

*Primary Examiner* — Jason Dunham
*Assistant Examiner* — Amber A Misiaszek
(74) *Attorney, Agent, or Firm* — Steven A. Bern

(57) ABSTRACT

A method of creating a classification system for rating the nature and severity of health care requirements, including obtaining a set of medical disease codes, categorizing the medical disease codes into major disease categories, and categorizing the medical disease codes in each major disease category into episode disease categories based on severity.

21 Claims, 4 Drawing Sheets

(56) References Cited

OTHER PUBLICATIONS

Ash A., et al., "Risk Adjustment for the Non-Elderly," Report supported by a grant from the Health Care Financing Administration (HCFA), Contract No. 18-C-90462/1-02, Sep. 4, 1997.

Bertko, J., Hunt, S., "Case study: The Health Insurance Plan of California," *Inquiry* 35 (2) Summer 1998 148-153.

Carter, G. M., Jacobson, J.D., Kominski, G. F., and Perry, M.J., "Use of Diagnosis-related Groups by Non-Medicare Payers," *Health Care Financing Review*, 16(2), 1994, 127-158.

Cumming, Robert B. and Cameron, Brian A., "A Comparative Analysis of Claims-Based Methods of Health Risk Assessment for Commercial Population", A research study sponsored by the Society of Actuaries, May 24, 2002. Web-site location: www.soa.org/ccm/cms-service/stream/asset?asset_id=9215098&g11n.

"DXCG and Risk Adjustment Bibliography", obtained from www.dxcg.com, published 2001.

"From Diagnosis Codes to Diagnostic Cost Groups", obtained from www.dxcg.com, Document data originally reported and published from 1986 to 1999.

"Introduction to DCGs," published at http://www.dxcg.com/introduct.htm, Apr. 30, 1999.

Kronick, R., Ph.D., Dreyfus, T., M.C.P., Lee, L., M.S., and Zhou, Z., Ph.D., "Diagnostic Risk Adjustment for Medicaid: The Disability Payment System," *Health Care Financing Review*/Spring 1996/vol. 17, No. 3, 7-33.

Kronick et al., "Improving Health-Based Payment for Medicaid Beneficiaries: CDPS," Health Care Financing Review, Spring 2000, vol. 21, No. 3, pp. 29-64.

Pope, G., Liu, C., Ellis, R. and Ash, A., et al., "Principal Inpatient Diagnostic Cost Group Models for Medicare Risk Adjustment," Appendix 2, *Health Economic Research*, Jan. 1999.

Pope, G., et al., "Revised Diagnostic Cost Group (DCG)/Hierarchical Coexisting Conditions (HCC) Models for Medicare Risk Adjustment," Final Report, Health Economics Research, Inc., Waltham, MA, prepared for Health Care Financing Administration, Feb. 6, 1998.

Terms and Definitions of ICD-9 codes obtained from http;//svr-www.eng.cam.ad.uk/projects/qamc/Terms.html. Document data originally published in 1975.

"What are ACGs," published at http://acg.jhsph.edu/what/what.html, Apr. 30, 1999.

\* cited by examiner

US 8,571,892 B2

METHOD OF GROUPING AND ANALYZING CLINICAL RISKS

CROSS REFERENCE TO RELATED APPLICATIONS

This application is a divisional of U.S. Ser. No. 09/302,336, filed Apr. 29, 1999, now U.S. Pat. No. 7,127,407, the disclosure of which is herein incorporated by reference.

STATEMENT OF GOVERNMENT RIGHTS

This invention was made with United States Government support under Cooperative Agreement Award no. 70NANB5H1013 awarded by the National Institute of Standards and Technology. The United States Government has certain rights in the invention.

BACKGROUND OF THE INVENTION

1. Technical Field

The present invention relates to risk/cost analysis tools for estimating future health care costs, and in particular to tools for retrospective review and profiling to create risk groups.

2. Description of the Related Art

Estimates of the anticipated health care requirements and costs for a group of patients may be used for a variety of purposes, most notably anticipating costs for insurance and other purposes related to the financing of health care. Estimates typically are made by analyzing the historical records of the members of the population for which the estimate is being made and extrapolating future health care requirements from clinical and other defined characteristics of the population. Systems for doing this are generally referred to as risk adjusters, since they categorize individuals based on their future risk for needing health care services. However, the risk adjusters to date have operated only at a high level, with the result that their efficacy and utility is limited.

In early risk adjusters, weights were calculated for each of a set of diagnostic categories and/or cost groups using a linear regression model. Only a single category, the most expensive, is chosen to estimate an individual's future costs and all other diagnoses are ignored. While a single factor clearly is inadequate for individuals with multiple problems, an additive approach is occasionally used. Currently available products, such as Hierarchical Coexisting conditions (HCC), determine the weight given each disease group using a linear regression model which assigns a weight for each of a set of diagnostic categories. Then, where and when applicable, the weights for each diagnostic category in an individual's history are added to get a total weight. The total weight is converted into a predicted cost for the next year. Additive approaches, however, may also not accurately represent the relationship between ostensibly independent problems. For example, consider the case of individuals with diabetes and hypertension, which generally are considered independent but interactive disease processes. While diabetes does not cause hypertension, or vice versa, it is not unusual for an individual to have both. However, the additional or marginal cost for treating a diabetic with hypertension may actually be considerably less than simply adding the cost for treating a non-hypertensive diabetic to the cost for treating a non-diabetic hypertensive. This makes intuitive sense when one considers that the diabetic already is making regular office visits for the diabetes, blood pressure is routinely checked during any medical office visit, so the costs are likely not equal to the costs of treating diabetes and hypertension independently.

Some past risk adjustment systems (e.g., the Medicare Diagnosis Related Groups, or DRGs) include some historical indication of overall severity at a particular time in a particular setting, but they do not explicitly identify severity by category of disease or project its likely impact upon medical needs into the future. The severity level of a disease can directly affect how that disease interacts with other diseases, and the consequent need for future care. To continue with the example just described, the example probably is true for low severity diabetes and low severity hypertension, but the opposite may be true for high severity diabetes and high severity hypertension. When both diseases are high severity, they can interact, making both diseases harder to treat. A system not explicitly incorporating severity into its logic will not identify this interaction risk.

Estimating costs using weights reflecting individuals from different points in the disease process also can be misleading. Individual health care needs vary not only by disease, but also by severity of disease. For example, at least in its early stages, hypertension is a relatively minor condition for many people, controllable by diet and exercise. However, for people in more advanced stages, it may be a fairly serious problem. It may require aggressive treatment, including occasional hospitalization, as well as posing a high risk of other significant cardiovascular problems. A single weight will not accurately reflect the severity of a disease experienced by individuals at different stages of the disease. No current risk adjustment system explicitly identifies levels of severity of disease.

Current systems also ignore the temporal aspects of care, such as treatment which may eliminate prior problems. For example, a patient with angina who undergoes a coronary arterial bypass graft (CABG) would not be expected to experience a recurrence of angina in the period following the bypass. But current systems do not take this into account—if angina has been recorded at any time, they continue to assume angina is present until such time as it no longer appears in the data.

The current systems, such as that in U.S. Pat. No. 5,557,514, were designed to predict future costs to allow calculation of insurance rates and identification of providers with high utilization profiles, but are of limited value to in helping providers to actually control costs. The capitated payment arrangements typical of health maintenance organizations and preferred provider organizations place the majority of financial risk on the providers of care. The underlying assumption is that since providers are responsible for the delivery of care, they can respond to the incentives to control costs inherent in a capitated payment system.

The success of any payment system that is predicated on providing incentives for cost control is almost totally dependent on the effectiveness with which the incentives are communicated to providers. Payers need to express the payment arrangements in a form that communicates the incentives in the system in a manner and at a level of detail that promotes effective management responses.

But detailed clinical descriptions are not considered in current systems, and, more importantly, explicit severity levels and interactions among clinical conditions are not a part of a group assignment. Therefore, data from such systems is of limited value to clinicians, who need to understand the clinical basis of their costs in order to respond effectively to incentives inherent in capitated payment systems. While it sometimes is possible to use the information from such risks adjuster to identify where pro-active efforts could substantially reduce problems (and costs), it is very difficult.

SUMMARY OF THE INVENTION

In one aspect, the present invention provides a method of creating a classification system for rating the nature and severity of health care requirements, including obtaining a set of medical disease codes, categorizing the medical disease codes into major disease categories, and categorizing the medical disease codes in each major disease category into episode disease categories based on severity. This method further includes sub-dividing at least some of the episode disease categories by severity of illness level by using severity of illness rules to take into account other episode disease categories or other information not related to a particular episode disease category being subdivided and defining criteria for assigning an overall clinical risk group to an individual patient, where the criteria takes into account the episode disease categories and severity of illness levels, where the criteria adjusts for the effect of interacting conditions in different episode disease categories.

In another aspect, the present invention provides a method of creating a classification system for rating the nature and severity of health care requirements, including obtaining a set of medical disease codes, categorizing the medical disease codes into major disease categories, and categorizing the medical disease codes into episode disease categories in each major disease category based on severity. This method further includes obtaining a set of medical procedure codes, categorizing the medical procedure codes into episode procedure categories, and sub-dividing at least some of the episode disease categories by severity of illness level by using severity of illness rules, wherein the severity of illness rules take into account temporal information including order of occurrence of the episode disease categories and episode procedure categories.

In another aspect the invention provides a method of creating a classification system for rating the nature and severity of health care requirements, including first, obtaining a set of medical disease codes and second, categorizing the medical disease codes into major disease categories, wherein each major disease category corresponds to a single organ system, a malignancy or a multiple trauma. The method further includes third, categorizing the medical disease codes in each major disease category into episode disease categories based on severity and fourth, sub-dividing at least some of the episode disease categories by severity of illness level by using severity of illness rules, thereby defining a set of severity of illness levels for each episode disease category.

The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

The preferred embodiments of the invention will be described in connection with the drawings, in which.

DETAILED DESCRIPTION OF THE PREFERRED EMBODIMENTS

Figure 1:
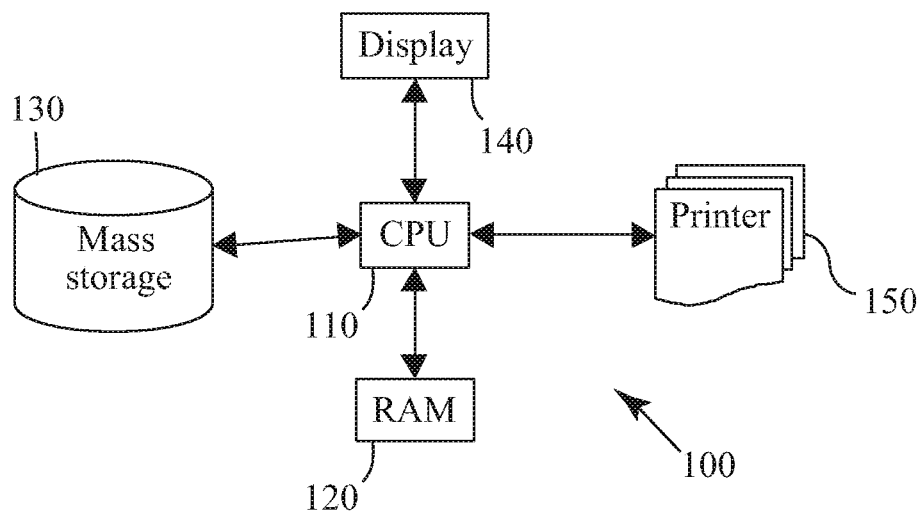
FIG. 1 is a schematic of a computer system by which the method of the present invention might be implemented.

The present invention creates a comprehensive set of risk groups which in particular explicitly identifies groups of individuals with multiple interacting co-morbid conditions, and which explicitly identifies the severity of illness level. This allows accurate prediction of future health care resource needs of an entire population, while simultaneously helping the health care provider isolate problems to identify changes in care to reduce costs and improve quality.

The present invention starts this process by developing a classification system that rates both the nature and severity of health care requirements, then applies that system to historical information for both individual patients and populations to group them according clinical risks. Each individual will fall into a single, mutually exclusive risk group in the classification system. Each risk group relates the historical clinical and demographic characteristics of the individual to the amount and type of health care resources that individual likely will consume in the future. Since the clinical risk groups are clinically based, they create a system that links the clinical and financial aspects of care. Thus, the clinical risk groups are designed to serve as the foundation of management systems which support care pathways, product line management and case management.

The present invention assumes there is at least one set of medical care codes available which is used to describe patient treatment. According to the present invention, the classification system is created by categorizing the medical care codes into major disease categories, and subdividing each major disease category into a plurality of episode disease categories based on the severity and/or longevity of the disease. The episode disease categories within each major disease category are ranked in seriousness, with, e.g., chronic diseases (e.g., emphysema) rated more severely than acute diseases which by their nature usually will last only a short while (e.g., pneumonia). In addition, severity of illness levels preferably are defined for episode disease categories.

In the typical situation, there in fact will be multiple sets of medical care codes, e.g., one used by hospitals and one used by physicians. Each of them can be categorized into its own sets of categories, though the level of detail applied may vary by set. For example, hospitals tend to have a far larger number of codes than physicians, so a more detailed categorization would be appropriate.

The classification system is applied to a set of historical data for an individual patient by first identifying all episode disease categories experienced by that individual. The episode disease categories within each major disease category are then adjusted to take into account to take into account the nature and timing of treatment events. For example, an individual with a history of angina, who then has angioplasty, can be expected to not have angina in the future. The episode disease category for angina therefore should be deleted, unless the angina has recurred some significant period of time (e.g., 90 days) after the angioplasty. Note that the information from multiple sets of codes may interact in this adjustment (e.g., angina often will be identified from physician records, while angioplasty will normally be identified from hospital records). The severity of illness is adjusted in a similar manner.

Once the episode disease categories have been defined and severity of illness adjusted, the primary chronic disease is identified for each major disease category. The severity of illness for each major disease category typically will be the same as that for the primary chronic disease, but may need to be adjusted if there are episode disease categories in other major disease categories which interact with it, e.g., amputation of extremities implies that a patient with diabetes is in an extremely advanced state of diabetes, which may be even worse if the patient also has congestive heart failure.

The major disease categories and their respective severity of illnesses then are aggregated in a similar fashion to identify a single clinical risk group for the individual, and an overall severity of illness for the individual.

The classification system then also defines a method for aggregating information about groups of patients, to allow the summation of information about large numbers of patients. Preferably, this involves grouping the clinical risk groups into aggregated clinical risk groups at a variety of levels.

A significant advantage to the present invention is that it allows health care providers to identify and pro-actively treat health problems. Unlike present capitation rate calculation systems, the clinical risk groups developed and used according to the present invention directly communicate information in a form and at a level of details that can lead to specific positive actions. To illustrate the difference, suppose that for individuals with diabetes the capitated payments are 25% lower than the provider's expenditures. While this is obviously useful information for identifying a problem, it does not give the provider any real information on the precise source of the problem, or the actions that can be taken to correct the problem. In contrast, suppose the payment system also provided the following information:

"The higher costs for diabetic individuals are due to unusually high expenditures for inpatient care combined with uncommonly low expenditures for pharmacy and outpatient laboratory services for severity of illness level 1 and 2 diabetic individuals. Further a higher than expected percentage of severity of illness level 1 and 2 diabetic individuals over time become severity level 3 or 4."

Clearly, the above information raises specific questions concerning the monitoring and preventive care being provided to individuals with low severity diabetes, which gives providers a basis for management action, and an effective response to the incentives in the payment system.

Another significant advantage of the present invention is that it allows much more accurate estimations of future health care needs and costs. Given a large sample size, it is quite straightforward to determine the typical future costs for each individual in a particular clinical risk group. Those costs then can be used to weight the total cost of a group, based on the number of individuals in each clinical risk group. Similarly, the clinical risk group information can also be used to develop much more accurate predictions of future capital equipment needs, personnel needs and the like.

Almost all payers for health care (the government, insurance companies, self-insured companies, etc.) require providers to report on the services for which they are seeking reimbursement using coding schemes, thereby allowing the payers to process the requests for payment efficiently. Most hospitals use the International Classification of Diseases, 9th Revision, Clinical Modifications (ICD-9-CM), to code diagnoses, signs, symptoms, findings and other factors influencing health status. Most professional services and procedures performed in an ambulatory setting are reported using Current Procedural Terminology (CPT) codes and the Health Care Financing Administration (HCFA) Common Procedure Coding Systems (HCPCS), which includes the CPT codes. The present invention therefore will be described with reference to the ICD-9-CM, CPT and HCPCS codes. However, it will be understood that the present invention could be used with any other suitably detailed coding scheme, and that these coding systems are being used simply because they will be familiar to one of skill in the art.

The present invention analyzes coded medical histories into Clinical Risk Groups (CRGs). Almost of necessity given the size of the databases involved, the process will be implemented in a computer-based system such as that shown in FIG. 1. In FIG. 1, the computer system 100 includes a central processing unit (CPU) 110, random access memory (RAM) 120, mass storage device 130 (such as a hard drive, CD drive, diskette drive or the like), a display 140 (such as a cathode ray tube, LED, LCD or plasma display) and a printer 150 (such as a dot matrix printer, a laser printer, or an ink jet printer), associated such that the CPU can read and write to the RAM 120 and the mass storage device 130, can control the images on the display 140 and the output of the printer 150.

The computer system 100 implements the CRG clinical logic based on a five step or phase process:

Phase I A disease profile and history of past medical interventions is created.

Phase II In each organ system, the most significant chronic disease under active treatment is identified Phase III In each organ system, the severity of illness level of the most significant chronic disease under active treatment is determined Phase IV The most significant chronic disease under active treatment and its associated severity of illness level are combined to determine the overall Base CRG and severity of illness level for the individual Phase V The overall Base CRG and severity of illness level are consolidated into three successive tiers of aggregation As will be seen, the five phase process for determining the CRG assignment identifies individuals with multiple interacting co-morbid diseases and their associated severity of illness level.

Classifications:

The present invention requires creation of a series of classifications, which are generated iteratively—set up a classification, run test data, analyze the results, modify the classification and repeat. There is no one correct set of classifications—the particular classifications will change with advancing medical knowledge and other changes affecting the practice of medicine. Therefore what will be described is the process of creating such a classification system.

In the ICD-9-CM, the term disease is used to encompass diagnoses, signs, symptoms, findings and other factors influencing health status. There are approximately 12,000 codes in the current version of ICD-9-CM. For brevity the ICD-9-CM codes will be referred to simply as disease codes.

Figure 2:
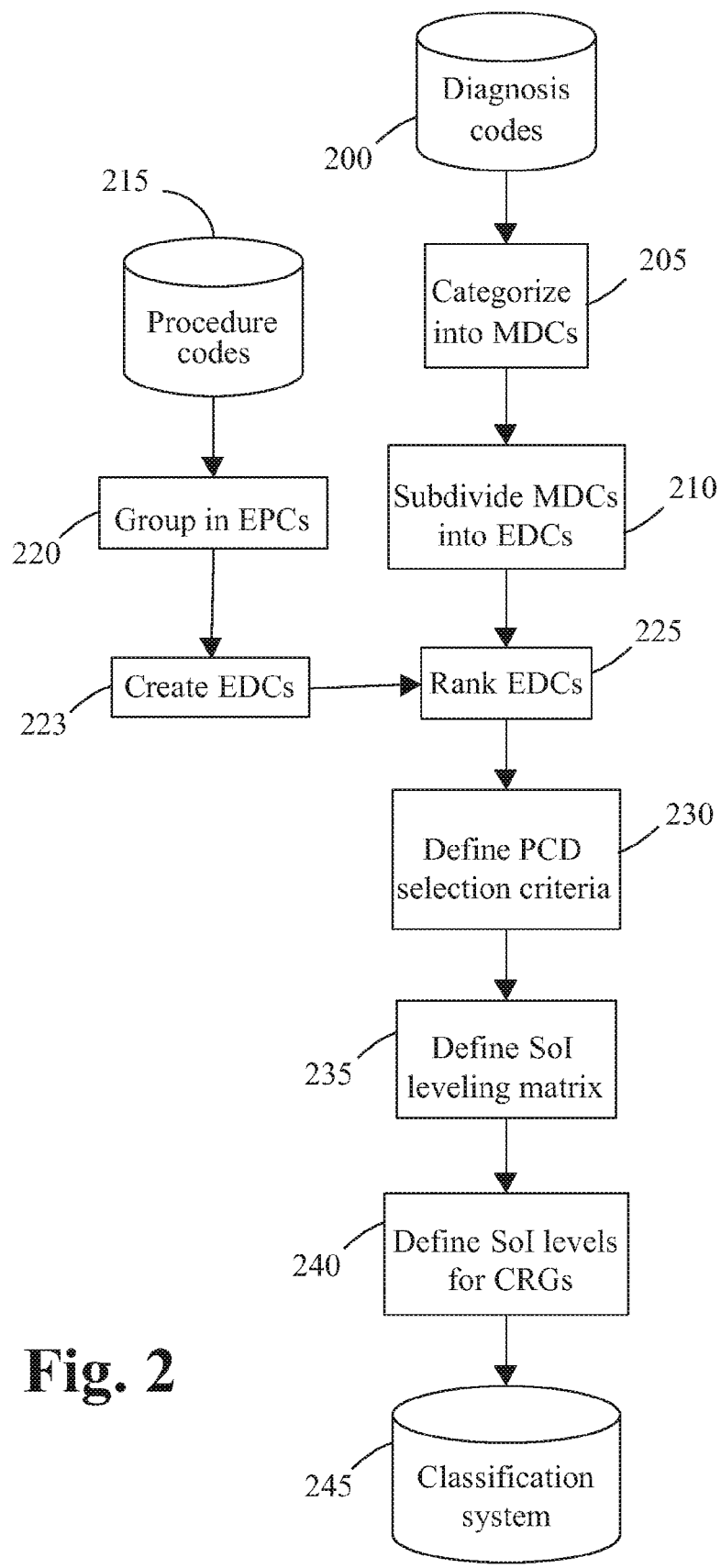
FIGS. 2-4 are flow charts schematically illustrating the steps of the preferred embodiments of the present invention.

Starting with step 200 in FIG. 2, each of the disease codes in the ICD-9-CM are categorized in step 205 into a series of mutually exclusive and exhaustive categories referred to as Major Disease Categories (MDCs). The diseases in each MDC correspond to a single organ system (e.g., respiratory system, digestive system, etc.) or etiology (e.g., malignancies, systemic infectious diseases, etc.). With the exception of malignancies and multiple trauma, which are each assigned to their own MDC, diseases that include both a particular organ system and a particular etiology (e.g., pneumonia) are assigned to the MDC corresponding to the organ system involved. Systemic infections such as septicemia, are assigned to the systemic infections disease MDC. Some diagnoses are considered catastrophic (e.g., persistent vegetative state) and are assigned to a catastrophic MDC. An example of a set of 31 MDCs meeting these criteria is shown in Table 1.

TABLE 1

List of MDCs

| Class | Description |
|---|---|
| 1 | Nervous System Diseases |
| 2 | Eye Diseases |
| 3 | Ear, Nose, Mouth And Throat Diseases |
| 4 | Cranial Facial Anomalies |
| 5 | Respiratory Diseases |
| 6 | Heart And Cardiac Vascular Diseases |

TABLE 1-continued

List of MDCs

| Class | Description |
|-------|-------------|
| 7 | Peripheral And Non-Cardiac Vascular Diseases |
| 8 | Digestive Diseases |
| 9 | Hepatobiliary & Pancreas Diseases |
| 10 | Musculoskeletal Diseases |
| 11 | Connective Tissue Diseases |
| 12 | Skin, Subcutaneous Tissue & Breast Diseases |
| 13 | Diabetes |
| 14 | Endocrine, Metabolic And Thyroid Diseases Except Diabetes |
| 15 | Kidney And Urinary Tract Diseases |
| 16 | Male Reproductive Diseases |
| 17 | Female Reproductive Diseases |
| 18 | Pregnancy, Childbirth And The Puerperium |
| 19 | Newborns And Other Neonates |
| 20 | Chromosomal Anomalies, Mental Retardation & Other Developmental Cognitive Diseases |
| 21 | Blood And Blood Forming Organ Diseases |
| 22 | Malignancies |
| 23 | Systemic Infectious And Parasitic Diseases |
| 24 | Mental Diseases |
| 25 | Substance Abuse |
| 26 | Injuries, Poisoning And Toxic Effects Of Drugs |
| 27 | Burns |
| 28 | Factors Influencing Health Status And Other Contacts With Health Services |
| 29 | HIV Infection |
| 30 | Multiple Significant Trauma |
| 31 | Catastrophic Conditions |

The diagnoses in each MDC are further subdivided into Episode Disease Categories (EDCs) in step 210. Each EDC is assigned to one of a number of EDC types, which rate the severity and persistence of the disease.

In a preferred embodiment, there are six EDC types. Four of the EDC types relate to chronic diseases and two of the EDC types relate to acute diseases. A disease is classified as chronic if the duration of the disease is life long (e.g., cystic fibrosis). Diseases which have a prolonged duration, but for which a cure (i.e., no evidence of the disease) is possible, are considered chronic (e.g., malignancies). Life long or prolonged diseases controlled by medication or other means (e.g., hypertension) are also considered chronic. A disease is classified as acute if the duration of the disease is short and the disease would naturally resolve (e.g., pneumonia) or there is a treatment which cures the disease (e.g., fractured leg). Signs, symptoms and findings (e.g., chest pain) in general are considered acute, even though they might be indicative of a chronic problem. The six preferred EDC types are defined as follows:

Dominant Chronic EDCs: Serious chronic diseases which usually result in the progressive deterioration of an individual's health and often times lead to, or significantly contribute to an individual's need for medical care, debility and death. (e.g., congestive heart failure, diabetes).

Moderate Chronic EDCs: Serious chronic diseases which, usually do not result in the progressive deterioration of an individual's health but can significantly contribute to an individual's need for medical care, debility and death (e.g., asthma, epilepsy).

Minor Chronic EDCs: Chronic diseases which may be serious in their advanced stages or may be a precursor to more serious diseases (e.g., hyperlipidemia), but can usually be managed effectively throughout an individual's life with few complications and minimal effect upon an individual's need for medical care, debility and death (e.g., migraine headache, hearing loss).

Chronic Manifestation EDCs: A manifestation or acute exacerbation of a chronic disease (e.g., diabetic neuropathy).

The chronic manifestation EDC describes manifestation or acute exacerbation (i.e., the neuropathy) and indicates the presence of the underlying chronic disease (i.e., diabetes). In addition, they are used to identify uncommon, but distinct, disease within a more frequently occurring EDC and are used to determine the severity level of the EDC, and for management reporting.

Significant Acute EDCs: Serious acute illness which can be a precursor to or place the individual at risk for the development of chronic disease (e.g., chest pain) or can result in significant sequelae (e.g., head injury with coma).

Minor Acute EDCs: Minor acute illnesses are self limiting, are not a precursor to chronic disease, do not place the individual at risk for the development of chronic disease and do not result in significant sequelae (e.g., fractured arm, common cold).

The categorization of an EDC as chronic or acute is an important distinction because individuals who have chronic EDCs from multiple organ systems (i.e., MDCs) are assigned to a distinct set of CRGs. Some diseases that are generally considered chronic can, under certain conditions, be an acute disease. For example, congestive heart failure is generally considered a chronic disease. However, congestive heart failure that occurs in children is usually associated with an underlying congenital anomaly which can be corrected by surgery. Therefore, in children congestive heart failure typically would be considered an acute disease. But even this has an exception if the congestive heart failure is due to rheumatic fever, which would always be considered chronic. Similarly, hypertension is generally considered a chronic disease. However, because there is the possibility that a single high blood pressure reading could be miscoded as hypertension, hypertension is considered an acute disease unless the hypertension recurs at least twice over a period of time that spans at least 90 days. Thus, some diseases generally considered chronic are only categorized as chronic under certain conditions.

As noted above, procedures performed in hospitals usually are reported using ICD-9-CM procedure codes. Professional services, and procedures performed in an ambulatory setting typically are reported more often as the Current Procedural Terminology (CPT) codes. Prescription drug usage may also be reported in a coded fashion. Like ICD-9-CM codes, at step 215 such procedural codes can be categorized in step 220 according to the present invention into mutually exclusive and exhaustive categories, referred to as Episode Procedure Categories (EPCs). The EPCs can be used to identify individuals who are dependent on some medical technology (e.g., dialysis), who had a procedure that is indicative of advanced disease (e.g., leg amputation) or who had a procedure that has long term sequelae (e.g., heart transplant).

The occurrence of EPCs that are indicative of advanced disease or that have long term sequelae are used in step 223 to create a chronic EDC that specifies a history of the procedure (e.g., history of heart transplant). Normally, no distinction need be made between chronic EDCs associated with the history of a procedure (created in step 223) and chronic EDCs associated with a disease (created in step 210).

As will be apparent, there usually will be hundreds of mutually inclusive and exhaustive EDCs across all of the MDCs. The exact list of EDCs and which disease goes into which EDC will vary with both time and circumstances, and will constantly change over time with changes in medical practice and knowledge. A sample of a possible set of EDCs for the circulatory system is provided in table 2.

TABLE 2

EDCs for the Circulatory MDC

| Rank | Type | EDC |
|---|---|---|
| 1 | DC | Major Congenital Heart Diseases |
| 2 | DC | Moderate Congenital Heart Diseases |
| 3 | DC | Congestive Heart Failure |
| 4 | DC | Major Chronic Cardiac Diseases |
| 5 | DC | Cardiac Valve Diseases |
| 6 | DC | History of AMI |
| 7 | DC | Angina |
| 8 | MC | Atrial Fibrillation |
| 9 | MC | Cardiac Dysrhythmia |
| 10 | MC | History of CABG |
| 11 | MC | History of PTCA |
| 12 | MC | History of Cardiac Device |
| 13 | MC | Coronary Atherosclerosis |
| 14 | MC | Hypertension |
| 15 | C | Ventrical and Atrial Sept Defects |
| 16 | C | Minor Chronic Cardiac Diseases |
|  | CM | History of Defibrillator |
|  | CM | Unstable Angina |
|  | CM | Moderate Hypertension |
|  | CM | Myocardiopathy |
|  | CM | Pulmonary Hypertension |
|  | CM | Graft Atherosclerosis |
|  | SA | Cyanosis |
|  | SA | Ventricular Tachycardia |
|  | SA | Complete Heart Block |
|  | SA | Shock |
|  | SA | Cardiac Arrest |
|  | SA | AMI Except Subendocardial |
|  | SA | Hypotension |
|  | SA | Tachycardia/Palpitation |
|  | SA | Moderate Acute Cardiac Diseases |
|  | SA | Chest Pain |
|  | SA | Subendocardial AMI |
|  | SA | Minor Hypertension |
|  | SA | Pediatric CHF |
|  | MA | Atrial Flutter |
|  | MA | Cardiac Inflammation |
|  | MA | Minor Acute Cardiac Diagnoses |
|  | MA | Malfunction Coronary Bypass Graft |
|  | MA | Complications CV Device, Implant, Graft |
|  | MA | Malfunction CV Device, Implant, Graft |
|  | M | Malfunction Vascular Graft |

At step 225 the dominant, moderate and minor chronic EDCs are ranked hierarchically in terms of their relative contribution to an individual's need for medical care, debility and death. Chronic EDCs which result in progressive deterioration of an individual's health are ranked highest in the chronic EDC hierarchy. Table 2 contains the EDCs, the disease type and the chronic EDC rank for the heart and cardiac vascular system MDC.

Next, a process is defined in step 230 to select from the EDCs and EPCs the primary chronic disease (PCD) for each organ system (i.e., MDC), in step 235 a severity of illness (SoI) leveling matrix is created, and in step 240 SoI levels are defined for each CRG, resulting in the final classification system in step 245. The PCD, SoI leveling matrix and SoI levels will be discussed in more detail below.

After setting initial criteria for the classification system, the initial criteria preferably are tested against real data sets to determine their accuracy. For initial testing, one approach is to Base CRG/SoI assignments on the first year or two of data, then check how that correlates to expenditures in the third year of data. Since, in general, individuals with high healthcare expenditures have significant disease, future expenditures can stand at least initially as a proxy for the individual's clinical condition.

Ultimately, however, detailed reports should be produced which examine the impact of a wide range of clinical characteristics on individuals with specific disease and combinations of diseases. For example, a report might examine the impact on subsequent expenditures of pneumonia in an individual with emphysema, over the most recent six months, or having occurred multiple times. Analysis of these reports then should be fed back into the different categories and how they are adjusted.

While steps in creating the classification system have been defined in a particular order, it will be understood that many of them can be shuffled. For example, instead of first defining the MDCs, then sub-dividing them into EDCs, and developing SoI ratings for the EDCs, it is perfectly possible to first define the EDCs, then group them into MDCs, and develop the SoI ratings either before or after the grouping. The important point is that in the end the classification system has the necessary components, not the particular order in which they are created.

Figure 3:
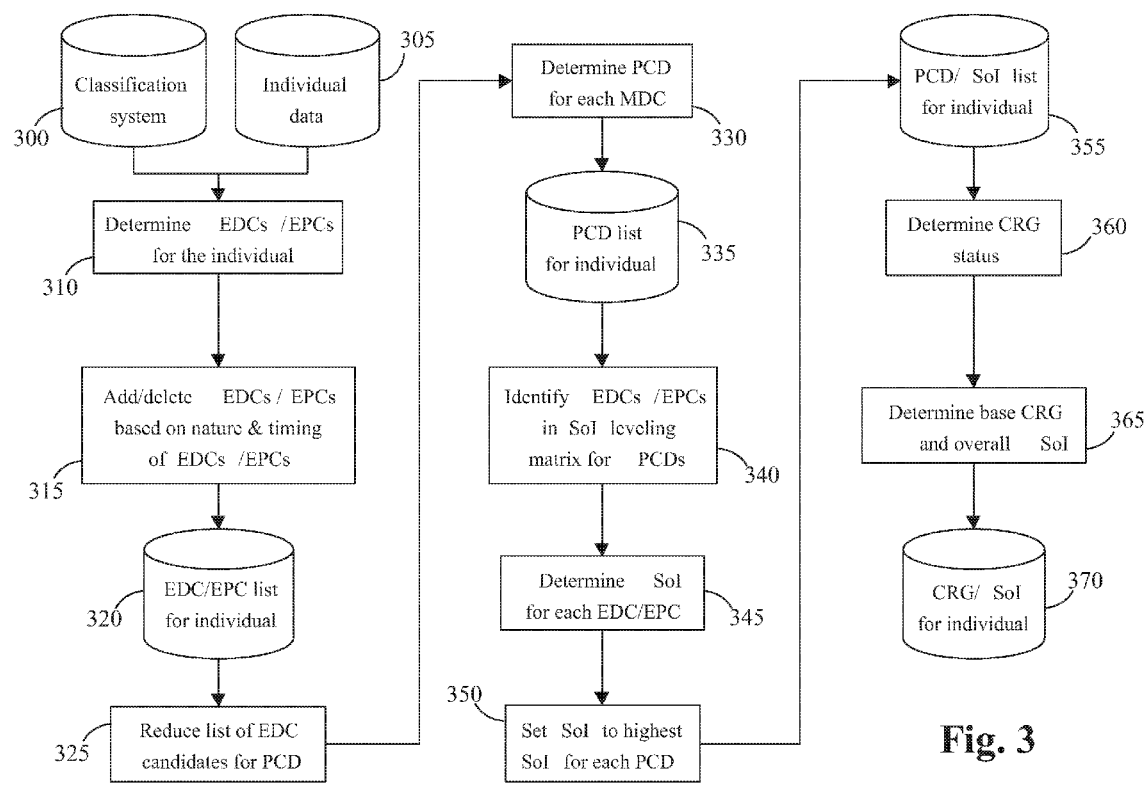
Figure 4:
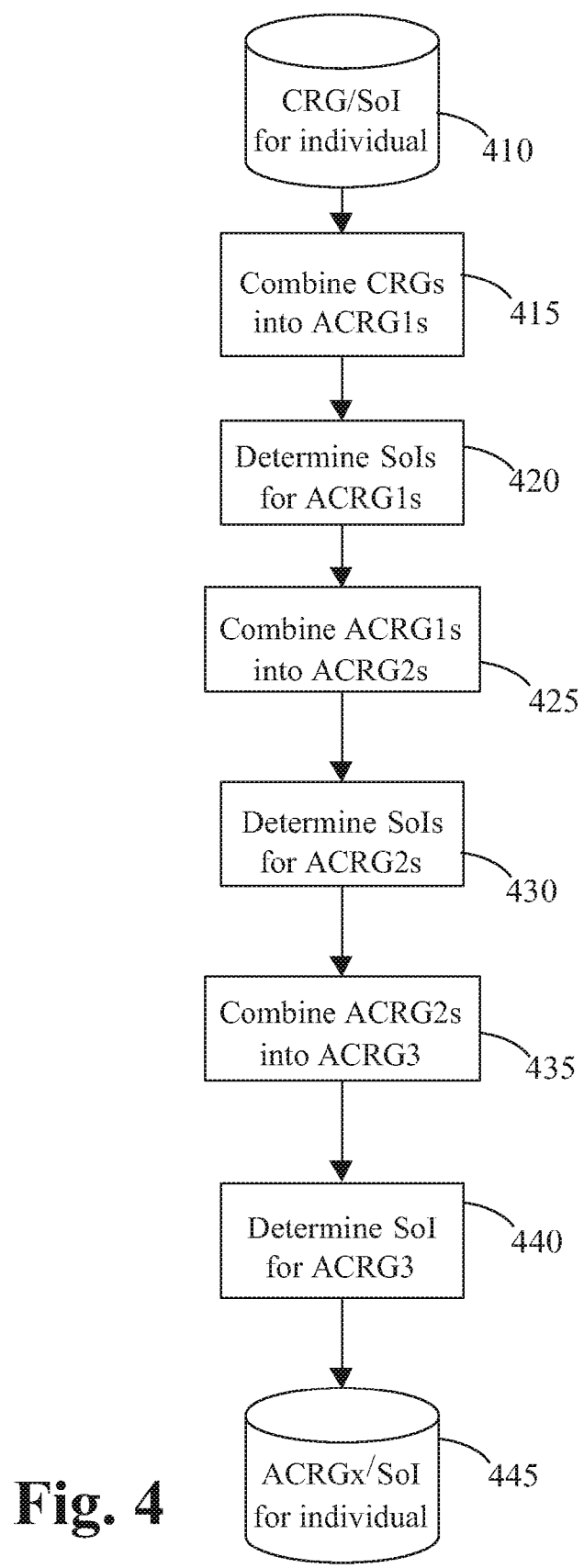

Phase I:

Phase I involves applying the various classifications in the classification system to the medical history of each individual in a group to define a chronic disease profile and history of past medical interventions for each individual. To start, refer to FIG. 3, where a classification system 300 (of the type which is the end result in step 245) is applied to a set of individual data 305 in step 310 to determine the EDCs and EPCs assigned to the individual, i.e., the EDCs and EPCs which code for medical care which has been provided to the patient at some time in the past.

Once the EDCs and EPCs have been assigned, EDCs and EPCs are added or deleted in step 315 based on the nature of and the temporal relationship among the EDCs and EPCs. There are a variety of ways in which these relationships are expressed. The crucial distinction is that this is done using clinically based conditionality which recognizes the interdependence of EDCs and EPCs. The process design for this step is such as to eliminate the impact of the order in which the conditions are considered, so as to ensure consistent results. One preferred way to do this is to start by creating EDCs, then to adjust for temporal effects and eliminate EDCs and EPCs which are clinically irrelevant. For example, as follows:

Create Chronic EDCs from Chronic Manifestation EDCs: All chronic manifestation EDCs create a chronic EDC that specifies the underlying chronic disease associated with the manifestation or acute exacerbation. For example, the diabetic neuropathy chronic manifestation EDC creates the diabetes EDC.

Create Chronic EDCs from Multiple Occurrences of an Acute EDC: Selected acute EDCs that have multiple occurrences over a period of time create a chronic EDC that indicates the recurrence of the acute EDC. For example, if the acute EDC for urinary tract infection occurs at least three times over a period of time that spans at least 180 days, the chronic EDC for recurrent urinary tract infection is created.

Significant Acute EDCs Create Chronic EDCs: Selected significant acute EDCs create a chronic EDC for the history of the significant acute EDC. For example, the significant acute EDC for AMI creates a chronic EDC for the history of the AMI. A history of a significant acute EDC is only created for significant acute EDCs that indicate a significant progression of an underlying disease (e.g., CVA) or have long term sequelae (e.g., hip fracture). The creation of a chronic EDC for the history of a significant acute EDC is sometimes dependent on the patient's age. The acute EDC for hip fracture only creates the chronic EDC for history of hip fracture if the individual is 65 years or older.

Major Procedure EPCs Create Chronic EDCs: Selected major procedures that are indicative of advanced disease or have long term sequelae create a chronic EDC for the history of the major procedure. For example, the EDC for coronary bypass surgery creates the chronic EDC for history of coronary bypass surgery.

Temporal Relationship Between EDCs: If specific EDCs occur prior to the first occurrence of another specified EDC, the EDC is eliminated. For example, if the CVA EDC occurs prior to the first occurrence of the hemiplegia EDC, the CVA EDC is eliminated because the hemiplegia is a sequelae of the CVA. However, if a CVA occurs after the first occurrence of hemiplegia, the CVA EDC is not eliminated since it represents a second CVA. The temporal relationship between CVA and hemiplegia is the basis for determining whether there has been a second CVA.

Temporal Relationship Between EDCs and EPCs: If specific EDCs occur prior to the occurrence of a specified EPC, the EDC will be eliminated. For example, if the angina EDC occurred prior to the coronary bypass EPC, the angina EDC is eliminated because the coronary bypass is expected to cure the angina. However, if angina occurs after the coronary bypass EPC, the angina EDC is not eliminated since it indicates that the coronary bypass was not successful.

Temporal Relationship Between EPCs: If a specific EPC occurs prior to the occurrence of another specified EPC, the EPC will be eliminated. For example, if a dialysis EPC occurs prior to a kidney transplant EPC, the dialysis EPC is eliminated because the kidney transplant is expected to eliminate the need for dialysis. However, if dialysis occurs after the kidney transplant EPC, the dialysis EPC is not eliminated since it indicates that kidney transplant was not successful.

The result of this Phase I analysis at step 320 is a complete list of EDCs and EPCs which describes each individual's disease profile and history of past medical interventions.

Phase II:

In Phase II, the EDC that represents the most significant chronic disease for which an individual is under active treatment, referred to as the primary chronic disease (PCD), is identified for each organ system (i.e., MDC).

An underlying assumption of the present invention is that individuals with co-morbid diseases from multiple organ systems constitute the individuals who have poor outcomes and require significant medical care. A single disease (i.e., EDC) therefore is selected from each major organ system (i.e., MDC) for the purpose of identifying the individuals with co-morbid disease in multiple organ systems.

The first step 325 in Phase II is to reduce the number of chronic EDCs in an MDC that are candidates to be the PCD. Certain chronic diseases are secondary to (i.e., a by-product of or an integral part of) another chronic disease. For example, when asthma and chronic bronchitis are both present, the chronic bronchitis is secondary to the asthma and the primary disease is asthma. In this example, chronic bronchitis is not assigned as the PCD if asthma is present.

The next step 330 in selecting the PCD is to eliminate from consideration as the PCD chronic EDCs that are secondary to another chronic EDC. If only one chronic EDC in an MDC remains after the chronic EDCs that secondary to another chronic EDC are eliminated, then that chronic EDC is the PCD for the MDC.

If more than one chronic EDC remains in the MDC, then the PCD selection criteria defined in step 230 are used to select the PCD. Table 3 provides an example of such a set of PCD selection criteria. In addition to the EDC type, the PCD selection criteria uses the site of service, recency and duration of treatment to select the PCD. An underlying assumption to this ranking is that the diseases that are under recent active treatment have the greatest impact on the subsequent need for medical care, debility and death.

TABLE 3

PCD Selection Criteria

| EDC Type | Site of Service | Recency of Treatment | Duration of Treatment |
|---|---|---|---|
| Dominant Chronic | Hospital | Last Year | |
| Dominant Chronic | Ambulatory | Last Year | 90 days |
| Dominant Chronic | | | |
| Moderate Chronic | Hospital | Last Year | |
| Moderate Chronic | Ambulatory | Last Year | 90 days |

The selection criteria in Table 3 are applied hierarchically from top to bottom. The chronic EDC that meets the highest criteria in the PCD selection hierarchy is selected as the PCD. If more than one EDC meets a selection criteria then the EDC rank in the MDC is used to select the EDC to be the PCD.

Within an EDC type, treatment in a hospital within the most recent year is highest in the selection hierarchy, followed by treatment in an ambulatory setting that had a duration of at least 90 days within the most recent year. Based on the PCD selection criteria, a moderate chronic EDC cannot be selected as the PCD if a dominant chronic EDC is present, and a minor chronic EDC can not be selected as the PCD if a moderate chronic EDC is present. However, within an EDC type, a lower ranking EDC can be selected as the PCD if it has been under active treatment in the past year.

At the end of Phase II, a list 335 of a PCD for each MDC that has at least one chronic EDC present has been determined.

Phase III:

In Phase III the PCD from each MDC is assigned a severity of illness level which for brevity, is referred to as the severity level or SoI. The severity level explicitly describes the extent and progression of the disease selected as the PCD. A high level of severity is indicative of poor prognosis, a high degree of treatment difficulty and a need for substantial medical care in the future.

The severity level of a PCD is determined based on the presence of other EDCs and EPCs. The severity level is primarily determined by the other chronic and acute EDCs that are present from the same MDC as the PCD. Chronic EDCs from other MDCs are used for severity leveling only when the EDC from the other MDC is, with a high degree of confidence, caused by the PCD. For example, malabsorption is caused by cystic fibrosis. Thus, the EDC associated with the malabsorption is used to assign the severity level for a cystic fibrosis PCD. Although a CVA is more likely to occur in an individual with diabetes, the diabetes does not cause the CVA and, therefore, the chronic EDC for history of CVA is not used to determine the severity level of a diabetes PCD.

Acute EDCs from any MDC are used to determine the severity level of the PCD. In particular, acute infections, neurological and gastrointestinal EDCs are used in the severity leveling as an indication of the general health status of the individual. The previous performance of a procedure associated with the treatment of the PCD is used in severity leveling when the procedure is indicative of advance disease or has long term sequelae.

Since any chronic EDC can be a PCD, all chronic EDCs have a severity leveling matrix, as defined in step 240. The severity leveling matrix consists of a list of EDCs and EPCs. Along with the list of EDCs and EPCs are the conditions or rules under which each EDC and EPC in the list results in a specific severity level. For example, an individual with a PCD of congestive heart failure who had been hospitalized with cardiac valve disease in the most recent year or had been treated at any site for a cardiac valve disease in the most recent six months is considered to have congestive heart failure at severity level 4. However, if the individual had cardiac valve disease, but had not been hospitalized for the cardiac valve diagnosis during the most recent year nor had been treated at any site for the cardiac valve disease during the most recent six months, then the individual is considered to have congestive heart failure at severity level 3. Thus, the severity level associated with the cardiac valve disease differs depending on conditions relating to recency of treatment and the site of treatment.

In addition to the recency and site of treatment, conditions used in the severity leveling matrices can relate to the duration of treatment or the age of the patient. Thus, there is a unique severity leveling matrix for each chronic EDC.

As an example, a severity leveling matrix for congestive heart failure is shown in Table 4. The EDCs at severity level 4 are primarily acute cardiac events (shock, cardiac arrest, acute myocardial infarction (AMI), unstable angina and ventricular tachycardia) that meet the condition of being recent or having required inpatient care. In addition, severity level 4 includes the recent occurrence of acute EDCs that are indicative of advanced congestive heart failure (pleural effusion and hypotension). Co-morbid cardiac diseases (cardiac valve disease, congenital heart disease, and major chronic cardiac diseases) that interact with the congestive heart failure and increase treatment difficulty are also included at severity level 4. Finally, EDCs and EPCs (tracheostomy) that relate to the dependence on a respirator are included at severity level 4.

TABLE 4

Severity Leveling Matrix For Congestive Heart Failure

| Severity Level | EPC | Type | Recency | Site | Duration |
|---|---|---|---|---|---|
| 4 | Cardiac Valve Diseases | DC | 2 Years | Inpatient | |
| 4 | Cardiac Valve Diseases | DC | 6 Months | | |
| 4 | Moderate Congenital Heart Diseases | DC | 2 Years | | |
| 4 | Major Congenital Heart Diseases | DC | 2 Years | Inpatient | |
| 4 | Major Chronic Cardiac Diseases | DC | 2 Years | Inpatient | |
| 4 | History of AMI | DC | 6 Months | | |
| 4 | Unstable Angina | CM | 1 Year | | 90 Days |
| 4 | Unstable Angina | CM | 1 Year | Inpatient | |
| 4 | Pleural Effusion | SA | 1 Year | | |
| 4 | Hypotension | SA | 6 Months | | |
| 4 | Shock | SA | 1 Year | | |
| 4 | Cardiac Arrest | SA | 1 Year | | |
| 4 | Ventricular Tachycardia | SA | 6 Months | | |
| 4 | Ventricular Tachycardia | SA | 1 Year | Inpatient | |
| 4 | Dependence on Respirator | MA | 1 Year | | |
| 4 | Permanent Tracheostomy | EPC | 2 Years | | |
| 4 | Temporary Tracheostomy | EPC | 2 Years | | |
| 3 | Cardiac Valve Diseases | DC | 2 Years | | |
| 3 | Major Congenital Heart | DC | 2 Years | | |
| 3 | Major Chronic Cardiac Diseases | DC | 2 Years | | |
| 3 | History of AMI | DC | 2 Years | | |
| 3 | Atrial Fibrillation | MC | 2 Years | | 90 Days |
| 3 | History of PTCA | MC | 2 Years | | |
| 3 | Cardiac Dysrhythmia | MC | 2 Years | | 90 Days |
| 3 | Cardiac Dysrhythmia | MC | 6 Months | | |
| 3 | Coronary Atherosclerosis | MC | 6 Months | | |
| 3 | Unstable Angina | CM | 1 Year | | |
| 3 | History of Defibrillator | CM | 2 Years | | |
| 3 | Graft Atherosclerosis | CM | 2 Year | | |
| 3 | Convulsions | SA | 1 Year | | 90 Days |
| 3 | Moderate Neurological SSFs | SA | 1 Year | | 90 Days |
| 3 | Extreme Neurological SSFs | SA | 1 Year | | 90 Days |
| 3 | Pulmonary Emboli | SA | 1 Year | | |
| 3 | Subendocardial AMI | SA | 1 Year | | |
| 3 | Thrombophlebitis | SA | 1 Year | | 90 Days |
| 3 | AMI Except Subendocardial | SA | 1 Year | | |
| 3 | Moderate Acute Cardiac Diseases | SA | 6 Months | | |
| 3 | Complete Heart Block | SA | 1 Year | | |
| 3 | Nausea, Vomiting & Diarrhea | SA | 1 Year | | 90 Days |
| 3 | Malfunction Coronary Bypass Graft | MA | 1 Year | | |
| 3 | Wheelchair | MA | 1 Year | | |
| 3 | Metabolic/Endocrine Diseases | MA | 6 Months | | |
| 3 | Mechanical Ventilation | EPC | 2 Years | | |
| 3 | Respiratory Therapy | EPC | 2 Years | | 90 Days |
| 3 | Hospital Bed | EPC | 2 Years | | |
| 3 | Wheelchair (Motorized) | EPC | 2 Years | | |
| 2 | Angina | DC | 2 Years | | |
| 2 | History of CABG | MC | 2 Years | | |
| 2 | Atrial Fibrillation | MC | 2 Years | | |
| 2 | Minor Chronic Artery & Vein Diseases | C | 1 Year | | 90 Days |
| 2 | Obesity | CM | 2 Years | | |
| 2 | Moderate Neurological SSFs | SA | 1 Year | | |

TABLE 4-continued

Severity Leveling Matrix For Congestive Heart Failure

| Severity Level | EPC | Type | Recency | Site | Duration |
|---|---|---|---|---|---|
| 2 | Extreme Acute Neurological Diseases | SA | 1 Year | | |
| 2 | Chest Pain | SA | 1 Year | | 90 Days |
| 2 | Hypotension | SA | 1 Year | Inpatient | |
| 2 | Significant GI Diagnoses | SA | 1 Year | | |
| 2 | Minor Acute GI Diagnoses | SA | 1 Year | | |
| 2 | Acute Pancreatitis | SA | 1 Year | | |
| 2 | Hypovolemia | SA | 1 Year | Inpatient | |
| 2 | Cellulitis | SA | 1 Year | | 90 Days |
| 2 | Major Infections | SA | 6 Months | | |
| 2 | Major Acute Mental Health Diseases | SA | 6 Months | | |
| 2 | High Mortality Acute Diseases | SA | 1 Year | | |
| 2 | Cardiac Inflammation | MA | 1 Year | Inpatient | |
| 2 | Atrial Flutter | MA | 1 Year | | |
| 2 | Acute Skin Diagnoses | MA | 1 Year | | 90 Days |
| 2 | Minor Bacterial Infections | MA | 1 Year | | 90 Days |
| 2 | Minor Infection | MA | 6 Months | | |
| 2 | Coronary Bypass | EPC | 2 Years | | |
| 2 | Major Cardiac Procedure | EPC | 2 Years | | |
| 2 | Permanent Cardiac Pacemaker | EPC | 2 Years | | |
| 2 | Oxygen Therapy | EPC | 2 Years | | |
| 2 | Walkers | EPC | 2 Years | | |
| 2 | Commode | EPC | 2 Years | | |
| 2 | Wheelchair (Standard) | EPC | 2 Years | | |
| 1 | Hypertension | MC | 2 Years | | |
| 1 | Cardiac Dysrhythmia | MC | 2 Years | | |
| 1 | History of Cardiac Device | MC | 2 Years | | |
| 1 | Coronary Atherosclerosis | MC | 2 Years | | |
| 1 | Ventrical and Atrial Sept Defects | C | 1 Year | | |
| 1 | Minor Chronic Cardiac Diseases | C | 1 Year | | |
| 1 | Chest Pain | SA | 1 Year | | |
| 1 | Cyanosis | SA | 1 Year | | |
| 1 | Minor Hypertension | SA | 1 Year | | |
| 1 | Pediatric CHF | SA | 1 Year | | |
| 1 | Tachycardia/Palpitation | SA | 1 Year | | |
| 1 | Moderate Acute Cardiac Diseases | SA | 1 Year | | |
| 1 | Malfunction CV Device, Implant, Graft | MA | 1 Year | | |
| 1 | Minor Acute Cardiac Diseases | MA | 1 Year | | |
| 1 | Complications CV Device, Implant, Graft | MA | 1 Year | | |
| 1 | Cardiac Inflammation | MA | 1 Year | | |
| 1 | Malfunction Vascular Graft | M | 1 Year | | |

Severity level 3 for congestive heart failure includes some of the same EDCs as level 4 (AMI, unstable angina, major chronic cardiac disease and congenital heart disease) but without the conditions of being recent or requiring inpatient care. Other moderate cardiac or circulatory EDCs are included at severity level 3 (complete heart block, cardiac dysrhythmia, thrombophlebitis, atrial fibrillation, coronary atherosclerosis, pulmonary emboli, history of coronary bypass and history of defibrillator). Recent acute endocrine, metabolic and neurological problems are also included at severity level 3 since they can be associated with advanced congestive heart failure. Finally, the presence of EPCs that are indicative of significant debility such as a hospital bed for the home or the need for a motorized wheelchair are included at severity level 3.

Severity level 2 for congestive heart failure includes some acute cardiac EDCs (chest pain, atrial flutter, stable angina and cardiac inflammation) plus some of the moderate cardiac or circulatory EDCs from severity level 3 (e.g., atrial fibrillation without the condition of having a duration of at least 90 days). Severity level 2 also includes a wide range of acute problems from other MDCs (e.g., infections, mental health diagnoses, skin diagnoses, etc.) that are indicative of general health status. Finally, an extended list of history of significant cardiac procedures (e.g., cardiac pacemaker) and EPCs related to medical supplies that are indicative of debility (e.g., walker, commode) are included at severity level 2.

If none of the EDCs and EPCs and associated conditions in severity levels 2 through 4 are present, then the congestive heart failure PCD is assigned severity level 1. For completeness, all the EDCs in the heart and cardiac vascular MDC that are not used in severity levels 2 through 4 are included in level 1 in the severity leveling matrix for congestive heart failure. However, since severity level 1 is the default severity level, a severity of level 1 can be assigned without any of the EDCs listed in level 1 being present.

The number of severity levels specified in the severity leveling matrix may vary across EDCs. Minor chronic EDCs and non-metastatic malignancy EDCs have only two severity levels specified because of the limited clinical spectrum of these diseases. All dominant chronic, moderate chronic and metastatic malignancy EDCs have four severity levels.

The severity level for a PCD is determined based on the following steps:

1. In step 340, use the complete list 320 of EDCs and EPCs created in Phase I to identify the subset of EDCs and EPCs that are present in the severity leveling matrix for the PCD.

2. In step 345, for each EDC and EPC identified in step 340, evaluate the associated conditions in the severity leveling matrix and determine the severity level for each EDC and EPC.
3. In step 350, set the severity level for the PCD equal to the highest severity level associated with any of the EDC and EPCs from step 345.

Since the same EDCs and EPCs can be used in the severity leveling matrix for PCDs in more than one MDC, it is possible that the same EDC or EPC could determine the severity level for more than one PCD. Thus, the presence of a single EDC or EPC could have a disproportionate impact on the overall severity level of the individual. To avoid this possibility, the severity level for each PCD preferably is determined in step 345 with the constraint that no EDC or EPC can determine the severity level (i.e., be the EDC or EPC used in step 3) of more than one PCD.

At the end of Phase III in step 355, all PCDs for an individual have been assigned a severity level.

Phase IV:

In phase IV, the PCD/SoI information is used to identify the CRG Status, Base CRG, and overall SoI. The CRG Status indicates a general overall status for the individual (e.g., anything from catastrophic to healthy). The Base CRG indicates the primary cause for the CRG status (e.g., Heart And Cardiac Vascular Diseases), while the overall SoI correlates to the severity of the Base CRG (e.g., in the hospital, ambulatory)

The individual is assigned to one of a number of CRG Statuses in step 360 based on the PCDs that are present. A preferred embodiment has 9 CRG Statuses:

Catastrophic Conditions: Catastrophic conditions include long term dependency on a medical technology (e.g., dialysis, respirator, TPN) and life-defining chronic diseases that dominate the medical care required (e.g., persistent vegetative state, cystic fibrosis, AIDS, history of heart transplant).

Dominant and Metastatic Malignancies: A malignancy that dominates the medical care required (e.g., brain malignancy) or a non dominant malignancy (e.g., prostate malignancy) that is metastatic.

Dominant Chronic Disease in Three or More Organ Systems: Dominant chronic disease in three or more organ systems is identified by the presence of three or more dominant PCDs.

Significant Chronic Disease in Multiple Organ Systems: Significant chronic diseases in multiple organ systems is identified by the presence of two or more PCDs of which at least one is a dominant or moderate PCD. PCDs that are a severity level 1 minor chronic disease are not considered a significant chronic disease and are not used to identify the presence of significant chronic disease in multiple organ systems.

Single Dominant or Moderate Chronic Disease: Single dominant or moderate is identified by the presence of a single dominant or moderate PCD.

Minor Chronic Disease in Multiple Organ Systems: Minor chronic disease in multiple organ systems is identified by the presence of two or more minor PCDs.

Single Minor Chronic Disease: A single minor chronic disease is identified by the presence of a single minor PCD.

History of Significant Acute Disease: A history of significant acute disease is identified by the presence of one or more significant acute EDCs in the last six months with no PCDs present.

Healthy: A healthy status is identified by the absence of any PCDs or recent significant acute EDCs or EPCs.

The CRG Status is assigned hierarchically starting with the catastrophic status. The first status in the hierarchy for which the status criteria are met is assigned as the CRG Status.

Once the CRG Status is determined, the Base CRG and overall severity level of the individual is determined in step 365. The Base CRG is assigned based on the PCD(s) which are present in the individual's record. The SoI in turn depends on the severity level of those PCDs, and where appropriate, any adjustments applied to the CRG status and Base CRG.

Catastrophic Conditions: The first status in the CRG status hierarchy is for individuals with catastrophic conditions associated with long term dependence on medical technology or life-defining chronic diseases that dominate the medical care required. All conditions that are considered catastrophic are ordered hierarchically (e.g., dialysis is higher in the catastrophic hierarchy than history of heart transplant). If there is more than one catastrophic condition present, the catastrophic condition that is highest in the catastrophic hierarchy is assigned as the Base CRG.

For each catastrophic condition there is a four level severity leveling matrix (defined in step 240) that is specific to the catastrophic condition. In addition, since individuals with a catastrophic condition can also have diseases in organ systems that are not directly related to the catastrophic condition, the severity level that is assigned based on the severity leveling matrix specific to the catastrophic condition is adjusted based on the presence of PCDs from organ systems unrelated to the catastrophic condition. The additional adjustment to the severity level is done to insure that the severity level of the catastrophic condition fully reflects to the total burden of illness.

Dominant And Metastatic Malignancies: The second status in the CRG status hierarchy is for individuals with dominant or metastatic malignancies. Certain malignancies (e.g., brain, pancreas, etc.) are similar to catastrophic conditions in that they are life defining and dominate the medical care required. Other malignancies (e.g., prostate, colon, etc.) do not dominate the medical care required unless they are metastatic. When multiple malignancies are present, each malignancy is classified as primary or secondary (e.g., a bone malignancy is considered secondary to a prostate malignancy). A primary malignancy is considered metastatic if there is a related secondary malignancy present.

In addition to identifying a primary metastatic malignancy by the presence of a related secondary malignancy, there are also some conditions that are indicative of an advanced stage of the primary malignancy and are, for all practical purposes, indicative of metastasis (e.g., malnutrition, the need for a second course of chemotherapy, etc.). For each dominant or metastatic primary malignancy there is a four level severity leveling matrix that is specific to the primary malignancy. In addition, since individuals with a dominant or metastatic primary malignancy can also have diseases in organ systems that are not directly related to the primary malignancy, the severity level that is assigned based on the severity leveling matrix specific to the primary malignancy is adjusted based on the presence of PCDs from organ systems unrelated to the primary malignancy. The additional adjustment to the severity level is done to insure that the severity level of the dominant or metastatic primary malignancy fully reflects the total burden of illness. Primary malignancies that are not dominant or metastatic are treated like any other disease and are included in the subsequent portions of the CRG status hierarchy.

Dominant Chronic Disease In Three Or More Organ Systems: The third status in the CRG status hierarchy is for individuals with dominant chronic diseases in three or more organ systems. Explicit combinations of three dominant PCDs are identified (e.g., congestive heart failure, diabetes and emphysema). The explicit combinations of three dominant PCDs are ranked hierarchically. Individuals with three or more dominant PCDs are assigned to a Base CRG that corresponds to the first match in the hierarchy. If the dominant PCDs do not match any of the explicit combinations, then the individual is assigned to a residual Base CRG that corresponds to any combination of three dominant PCDs that are not explicitly specified in the hierarchy.

Each Base CRG that is comprised of three or more dominant PCDs is subdivided in six severity levels. The severity level is determined using the severity level for each of the PCDs that comprised the CRG. Table 5 provides an example of a suitable matrix to assign the severity of illness.

TABLE 5

Severity Levels for CRGs Composed of Three or More Dominant PCDs

| CRG Severity Level | Severity Level of PCDs | | |
|---|---|---|---|
| | 4 | 3 | 2 or 1 |
| 6 | 3 or more | | |
| 5 | 2 | 1 or more | |
| 4 | 2 | None | 1 or more |
| 4 | 1 | 2 or more | |
| 3 | 1 | 1 | 1 or more |
| 3 | 1 | None | 2 or more |
| 3 | 1 | 3 or more | |
| 2 | | 2 | 1 or more |
| 2 | | 1 | 2 or more |
| 1 | | 1 | 3 |

The criteria in Table 5 are applied hierarchically from top to bottom. The severity level for the CRG is assigned based on the first criteria that is matched in Table 5. For example, if the three dominant PCDs that comprise the CRG have severity levels of 4, 4 and 2, then the severity level of the CRG would be 4. The severity level that results from Table 5 is generic to all CRGs, since the same Table 5 applies to all CRGs that are comprised of three more dominant PCDs.

The CRG severity level that results from the application of the generic criteria in Table 5 is then adjusted based on criteria that is specific to that Base CRG. The adjustments reflect that conditions become more complex in the presence of multiple disease processes, or the presence of other complication factors. For example, the generic severity level for the Base CRG comprised of congestive heart failure, diabetes and emphysema is increased by one if the EDC for unstable angina is present and the unstable angina has been actively treated in the most recent six month period. The unstable angina is often treated by performing coronary bypass surgery. However, if the patient also has diabetes and emphysema the surgical treatment may not be an option resulting in a difficult to treat patient with a probable poor prognosis.

Significant Chronic Disease In Multiple Organ Systems: The fourth status in the CRG status hierarchy is for individuals with significant chronic diseases in multiple organ systems. For individuals who do not have three or more dominant chronic diseases but do have multiple chronic diseases with at least one dominant or moderate chronic disease, explicit combinations of two PCDs are identified (e.g., congestive heart failure and diabetes). Severity level 1 minor PCDs are not used in identifying combinations of two significant chronic diseases since they have minimal impact on the individual's need for medical care.

The explicit combinations of two PCDs are ranked hierarchically. Individuals with two or more PCDs are assigned to a Base CRG that correspond to the first match in the hierarchy. If the PCDs do not match any of the explicit combinations, then a residual Base CRG is assigned that correspond to any combination of two PCDs that are not explicitly specified in the hierarchy.

Each Base CRG that is comprised of two PCDs is subdivided into between 2 and 6 severity levels. Since non-metastatic malignancy PCDs only have two severity levels and since minor PCDs at severity level 1 are not used in the combinations of two PCDs, the number of severity levels depend on the PCDs that comprise the combination. A combination that is comprised of a non-metastatic malignancy PCD and a severity level 2 minor PCD has two severity levels. A combination that is comprised of a dominant or moderate PCD and a severity level 2 minor PCD or a non-metastatic malignancy PCD has four severity levels. All other combinations of PCDs have six severity levels.

The severity levels for the CRG is determined using the severity level for each of the PCDs that comprise the combination. Since the individual PCDs that comprise the combination can be very different in terms of relative clinical significance (e.g., the combination of congestive heart failure and diabetes versus the combination of congestive heart failure and glaucoma) the criteria used to determine the severity level for the CRG is specific to the PCDs that comprise the combination. Table 6 shows the severity levels for a CRG composed of the dominant PCD for diabetes and the dominant PCD for congestive heart failure.

TABLE 6

Severity Levels for the CRG that is Comprised of the PCDs for Congestive Heart Failure and Diabetes

| Congestive Heart Failure Severity Level | Diabetes Severity Level | | | |
|---|---|---|---|---|
| | 4 | 3 | 2 | 1 |
| 4 | 6 | 5 | 4 | 4 |
| 3 | 5 | 4 | 3 | 3 |
| 2 | 4 | 3 | 2 | 2 |
| 1 | 3 | 2 | 2 | 1 |

Based on the criteria in Table 6, if the diabetes PCD is severity level 3 and the congestive heart failure PCD is severity level 4, the severity level for the CRG is 5.

The CRG severity level that results from the application of criteria like that in Table 6 is further adjusted based on criteria that is specific to that Base CRG. The adjustments reflect that conditions become more complex in the presence of multiple disease process, or the presence of other complication factors. For example, the CRG severity level for the Base CRG comprised of congestive heart failure and diabetes is increased by one if the PCD for chronic gastric ulcer is present and the chronic gastric ulcer has been actively treated in the most recent six month period. Since the gastric ulcer PCD is not a dominant chronic disease the individual is not assigned to one of the CRGs for three dominant chronic diseases. However, the chronic ulcer disease complicates the treatment of the congestive heart failure and diabetes and, therefore, increases the severity level.

Single Dominant Or Moderate Chronic Disease: The fifth status in the CRG status hierarchy is for individuals with a single dominant or moderate chronic disease. These individuals have only one PCD. The Base CRG is the same as the PCD (i.e., if the single PCD for the patient is diabetes, the Base CRG is diabetes). The severity level for the CRG is the same as the PCD severity level. The malignancy PCDs have two severity levels and all other moderate and dominant PCDs have four severity levels.

Minor Chronic Disease In Multiple Organ Systems: The sixth status in the CRG status hierarchy is for individuals with two or more minor chronic diseases. Individuals with two or more minor chronic diseases are assigned to a single Base CRG which has four severity levels based on the number of minor chronic PCDs present and the severity level of the minor chronic PCDs.

Single Minor Chronic Disease: The seventh status in the CRG status hierarchy is for individuals with a single minor chronic disease. These individuals have only one PCD. The Base CRG is the same as the PCD. The severity level for the CRG is the same as the PCD severity level.

History Of Significant Acute Disease: The eighth status in the CRG status hierarchy is for individuals with a history of significant acute disease. The individual has no PCDs present but at least one significant acute EDC is present. If the significant acute EDC (e.g., AMI) creates a chronic EDC for the history of the significant acute (e.g., history of AMI) then the individual would have a PCD present and, therefore, would not be assigned to the status for history of significant acute disease. Thus, individuals with significant acute diseases with significant sequelae such as AMI are not included in this status. However, the significant acute diseases that are present in this status can be a precursor to chronic disease or place the individual at risk for the development of chronic disease (e.g., chest pain). Thus, although the patients in the history of significant acute disease status do not have any chronic diseases, they are distinct from healthy individuals.

Certain EPCs are also considered equivalent to a significant acute disease. For example, if the skin graft EPC is present, the individual is assigned to the history of significant acute disease status even if no significant acute EDCs are present. The performance of a skin graft is considered indicative of a history of significant acute disease. There are a number of Base CRGs, e.g., six, for individuals with history of significant acute disease. The Base CRGs are determined based on the number and duration of the significant acute diseases present. There are no severity levels assigned to the history of significant acute disease CRGs.

Healthy: The ninth and final status in the CRG status hierarchy is for healthy individuals who have no PCDs and no significant acute EDCs or EPCs. They may have minor acute EDCs present (e.g., common cold) but are otherwise healthy. There is a single CRG for healthy individuals.

The end result of phase IV is a CRG/SoI for the individual, at 370. Individual CRG/SoI data can be used for a variety of purposes, most notably as a very shorthand description of the overall health condition of the individual, but are most useful when analyzed in groups, in phase V.

Phase V:

For higher level reports, it is useful to aggregate the CRG levels into smaller sets of risk groups. In step 410, the starting point for this is the CRG/SoIs developed for a an individual in phases I to IV. Phase V then consolidates the CRGs into successive tiers of aggregation, preferably three tiers. Each successive tier of aggregation has fewer Base CRGs. Across the CRG aggregations, the CRG Status and the severity levels within the aggregated CRGs are maintained. Thus, the successive tiers of CRG aggregation maintain the CRG Status and maintain the severity levels but reduce the number of Base CRGs.

Although the aggregation of CRGs reduces clinical precision, the successive tiers of aggregation maintain clinical meaningfulness (in contrast to past practices focussing just on cost). The successive tiers of aggregation take into consideration the future medical care needs and clinical similarity of the individuals assigned to the aggregated CRGs. The aggregated CRGs are referred to as ACRGs and the successive tiers of aggregation may be referred to with suitable designators, e.g., ACRG1, ACRG2 and ACRG3, with ACRG3 being the highest level of aggregation. Table 7 provides an example of summarizes the aggregation of CRGs into ACRGs.

TABLE 7

Aggregation of CRGs into ACRGs

| CRG Status | CRG | ACRG1 | ACRG2 | ACRG3 |
|---|---|---|---|---|
| Catastrophic | | | | |
| Base | 11 | 10 | 6 | 1 |
| SoI Levels | 4 | 4 | 4 | 6 |
| Total | 44 | 40 | 24 | 6 |
| Dominant and Metastatic Malignancies | | | | |
| Base | 23 | 3 | 1 | 1 |
| SoI Levels | 4 | 4 | 5 | 4 |
| Total | 92 | 12 | 5 | 4 |
| Dominant Chronic Disease in Three or More Organ Systems | | | | |
| Base | 21 | 7 | 2 | 1 |
| SoI Levels | 6 | 6 | 6 | 6 |
| Total | 126 | 42 | 12 | 6 |
| Significant Chronic Disease in Multiple Organ Systems | | | | |
| Base | 61 | 24 | 8 | 1 |
| SoI Levels | 2, 4, 6 | 4, 6 | 5, 6 | 6 |
| Total | 324 | 134 | 47 | 6 |
| Single Dominant or Moderate Chronic Disease | | | | |
| Base | 109 | 25 | 8 | 1 |
| SoI Levels | 2, 4 | 2, 4 | 2, 5, 6 | 6 |
| Total | 406 | 96 | 35 | 6 |
| Minor Chronic Disease in Multiple Organ Systems | | | | |
| Base | 1 | 1 | 1 | 1 |
| SoI Levels | 4 | 2 | 2 | 2 |
| Total | 4 | 2 | 2 | 2 |
| Single Minor Chronic Diseases | | | | |
| Base | 40 | 21 | 2 | 1 |
| SoI Levels | 2 | 2 | 2 | 2 |
| Total | 80 | 42 | 4 | 2 |
| History of Significant Acute Disease | | | | |
| Base | 6 | 1 | 1 | 1 |
| SoI Levels | 1 | 1 | 1 | 1 |
| Total | 6 | 1 | 1 | 1 |
| Healthy | | | | |
| Base | 1 | 1 | 1 | 1 |
| SoI Levels | 1 | 1 | 1 | 1 |
| Total | 1 | 1 | 1 | 1 |
| Total | | | | |
| Base | 273 | 93 | 30 | 9 |
| SoI Levels | 1, 2, 4, 6 | 1, 2, 4, 6 | 1, 2, 4, 5, 6 | 1, 2, 5, 6 |
| Total | 1083 | 370 | 131 | 34 |

In the example used in Table 7, the number of Base CRGs are 273, 93, 30 and 9 and the number of CRGs with severity levels are 1083, 370, 131 and 34 for CRG, ACRG1, ACRG2 and ACRG3, respectively.

The process of aggregating CRGs into successive tiers of ACRGs is illustrated in Table 8 for the CRG Status comprising dominant and moderate chronic diseases for the MDCs for heart and coronary vascular diseases, peripheral vascular and non-cardiac vascular diseases and respiratory diseases.

TABLE 8

Aggregation of Cardiopulmonary CRGs into ACRGs for the CRG Status Consisting of a Single Dominant or Moderate Disease

| | CRGs |
|---|---|
| | Heart and Coronary Vascular Diseases |
| | 13 Base CRGs × 4 SoI Levels = 54 |
| | CRGs |
| DC | Congestive Heart Failure |
| DC | Major Congenital Heart |
| DC | Moderate Congenital Heart |
| DC | Major Cardiac Diagnoses |
| DC | Cardiac Valve Diagnoses |
| DC | History of AMI |
| DC | Angina |
| MC | Atrial Fibrillation |
| MC | Cardiac Dysrhythmia |
| MC | History of CABG |
| MC | History of PTCA |
| MC | History of Cardiac Device |
| MC | Coronary Atherosclerosis |
| MC | Hypertension |
| | Peripheral and Non Cardiac Vascular Diseases |
| | 3 Base CRGs × 4 SoI Levels = 12 |
| | CRGs |
| DC | Peripheral Vascular Disease |
| DC | Moderate Artery and Vein Disease |
| MC | Leg Varicosities with Ulcer |
| | Respiratory Diseases |
| | 5 Base CRGs × 4 SoI Levels = 20 |
| | CRGs |
| DC | COPD and Bronchiectasis |
| DC | BPD/Major Lung Anomaly |
| DC | Significant Pulmonary Disease |
| DC | Tracheostomy Status |
| MC | Asthma |
| | ACRG1 |
| | Circulatory Diseases |
| | 4 Base ACRG1s × 4 SoI Levels = 16 |
| | ACRG1s |
| | Congestive Heart Failure |
| DC | Congestive Heart Failure |
| | Dominant chronic circulatory diseases except CHF |
| DC | Major Congenital Heart |
| DC | Moderate Congenital Heart |
| DC | Major Cardiac Diagnoses |
| DC | Cardiac Valve Diagnoses |
| DC | History of AMI |
| DC | Angina |
| DC | Peripheral Vascular Disease |
| DC | Moderate Artery and Vein Disease |
| | Moderate chronic circulatory diseases except hypertension |
| MC | Atrial Fibrillation |
| MC | Cardiac Dysrhythmia |
| MC | History of CABG |
| MC | History of PTCA |
| MC | History of Cardiac Device |

TABLE 8-continued

Aggregation of Cardiopulmonary CRGs into ACRGs for the CRG Status Consisting of a Single Dominant or Moderate Disease

| MC | Coronary Atherosclerosis |
|---|---|
| MC | Leg Varicosities with Ulcer |
| | Hypertension |
| MC | Hypertension |
| | Respiratory Diseases |
| | 2 Base ACRG1s × 4 SoI Levels = 8 |
| | ACRG1s |
| | Dominant chronic respiratory diseases |
| DC | COPD and Bronchiectasis |
| DC | BPD/Major Lung Anomaly |
| DC | Significant Pulmonary Disease |
| DC | Tracheostomy Status |
| | Asthma |
| MC | Asthma |
| | ACRG2 |
| | Cardiopulmonary Diseases |
| | 1 Base ACRG2 × 6 SoI Levels = 6 |
| | ACRG2s |
| DC | Congestive Heart Failure |
| DC | Major Congenital Heart |
| DC | Moderate Congenital Heart |
| DC | Major Cardiac Diagnoses |
| DC | Cardiac Valve Diagnoses |
| DC | History of AMI |
| DC | Angina |
| DC | Peripheral Vascular Disease |
| DC | Moderate Artery and Vein Disease |
| DC | COPD and Bronchiectasis |
| DC | BPD/Major Lung Anomaly |
| DC | Significant Pulmonary Disease |
| DC | Tracheostomy Status |
| MC | Atrial Fibrillation |
| MC | Cardiac Dysrhythmia |
| MC | History of CABG |
| MC | History of PTCA |
| MC | History of Cardiac Device |
| MC | Coronary Atherosclerosis |
| MC | Leg Varicosities with Ulcer |
| MC | Hypertension |
| MC | Asthma |

As shown in Table 8, in these three MDCs there are 24 Base CRGs, each with 4 severity levels for a total of 96 CRGs. In step 415, the CRGs are aggregated into ACRG1s by combining the MDCs for heart and coronary vascular disease together with the MDC for peripheral vascular and non-cardiac vascular disease into "circulatory diseases", which is subdivided into the following four circulatory base ACRG1s.

Congestive heart failure
Dominant chronic circulatory diseases except CHF
Moderate chronic circulatory diseases except hypertension
Hypertension Similarly, the CRGs in the respiratory system are aggregated into two base ACRG1s Dominant chronic respiratory diseases
Asthma Thus, the 24 Base CRGs from these three MDCs are consolidated into six base ACRG1s.

The severity level for the ACRG1 is determined in step 420. It is the same as the severity level for the CRG (e.g., if the severity for the angina CRG is level 3, the severity level for the ACRG1 for dominant chronic circulatory diseases except CHF is also level 3). Thus, the 96 CRGs in these three MDCs for the single dominant or moderate chronic disease status are aggregated into 24 ACRG1s.

In step 425, the six Base CRGs in ACRG1 are aggregated into a single ACRG2 for cardiopulmonary disease. However, because there is significant clinical diversity across the six ACRG1s, the number of severity levels in ACRG2 is expanded to six. The mapping of the four severity levels for the ACRG1s to the six severity levels for the ACRG2s is shown in Table 9.

TABLE 9

Mapping of ACRG1 Severity Level to ACRG2 Severity Level for Cardiopulmonary Diseases

| Base ACRG1 | ACRG2 severity Level | | | | | |
|---|---|---|---|---|---|---|
| | 1 | 2 | 3 | 4 | 5 | 6 |
| Congestive Heart Failure | | | 1 | 2 | 3 | 4 |
| Dominant Chronic Circulatory System Diseases except CHF | | 1 | 2 | 3 | 4 | |
| Dominant Chronic Respiratory Diseases | | | 1 | 2 | 3 | 4 |
| Moderate Chronic Circulatory System Diseases except Hypertension | 1 | 2 | 3 | 4 | | |
| Hypertension | 1 | 2 | 3 | 4 | | |
| Asthma | 1 | 2 | 3 | 4 | | |

Severity level 6 for cardiopulmonary base ACRG2 is composed of ACRG1 severity level 4 congestive heart failure and ACRG1 severity level 4 dominant chronic respiratory diseases. The mapping of the ACRG1 severity levels to the ACRG2 severity levels in step 430 reflects both the ACRG1 severity level and the relative clinical significance of the different base ACRG1s that are aggregated into a single base ACRG2.

In step 430, all base ACRG2s in the single dominant or moderate chronic disease status are aggregated into a single base ACRG3 with six severity levels. Similar to the severity level mapping between ACRG1 and ACRG2, in step 440, there is a severity level mapping between ACRG2 and ACRG3 that reflects the relative clinical significance of the different base ACRG2s that are aggregated into the single base ACRG3. The end result in step 445 is a set of ACRG/SoI ratings for the individuals using ever smaller sets of Base CRG categories.

The clinical logic in the five phase process for determining CRG assignment results in a severity adjusted set of mutually exclusive and exhaustive categories that differentiate the relative need for medical care as well as debility and death. The multiple aggregations of CRGs provide the flexibility for CRG to be used at a level of detail that corresponds to the needs of all users including payers and providers. Since the successive consolidations of CRGs are formed in a hierarchical manner, upper management can receive highly aggregated reports, while clinicians can receive a corresponding set of reports that contain more details.

The CRGs can be used in several ways to project future costs, by computing the average future cost of individuals assigned to each CRG, and weighting total costs for a group based on the number of individuals in each CRG. For example, suppose two years of historical data were available. CRGs would be assigned based on the demographic and clinical information in the first year. CRG payment weights would be computed as the average expenditures in the second year for individuals assigned to each CRG based on the first year data. Thus, the first year of data is used to assign the CRG and the second year is used to compute the CRG payment weight. The separation of the CRG clinical model and the CRG payment weights allows payers to compute their own payment weights while using the standard CRG clinical model.

The CRGs also are very useful in projecting costs for different mixes of coverage. The specific categories of expenditures included in capitated payment arrangements can vary. For example, pharmacy costs may be carved out of the capitated rate. The CRG payment weights can be expressed in terms of the cost components that make up the payment weight (e.g., pharmacy, physician, hospital, laboratory, etc.) so that the proportion of the payment weight that is associated with each cost component is known. For example, a capitated payment arrangement negotiated with a managed care organization might exclude pharmacy expenditures, which could be paid on a capitated basis to a separate organization. CRG payment weights excluding pharmacy and separate CRG pharmacy payment weights can be generated to support such a payment arrangement. The separation of the clinical model and payment weights, and the relatively straight-forward method for computing the CRG payment weights (i.e., the average values for each CRG) provides great flexibility in establishing capitated payment arrangements.

The multiple levels of aggregated CRGs also make the CRGs useful in calculating payment weights for relatively small groups. Payers that wish to compute their own payment weights but have relatively few covered individuals can use a highly consolidated tier of CRG aggregation in order to have a sufficient number of covered individuals in each ACRG to compute a payment weight.

It will be understood that these exemplary embodiments in no way limit the scope of the invention. Other modifications of the invention will be apparent to those skilled in the art in view of the foregoing description. These descriptions are intended to provide specific examples of embodiments which clearly disclose the present invention. Accordingly, the invention is not limited to the described embodiments or to the use of specific elements, dimensions, materials or configurations contained therein. All alternative modifications and variations of the present invention which fall within the spirit and scope of the appended claims are covered.

We claim:

1. A method of creating a classification system for rating the nature and severity of health care requirements, including:
   (a) a computer system obtaining a set of medical disease codes;
   (b) categorizing the medical disease codes into major disease categories using the computer system;
   (c) categorizing the medical disease codes in each major disease category into episode disease categories based on severity of health care requirements using the computer system;
   (d) sub-dividing at least some of the episode disease categories using the computer system by severity of illness level by using severity of illness rules to take into account other episode disease categories or other information not related to a particular episode disease category being subdivided; and
   (e) defining criteria using the computer system for assigning an overall clinical risk group to an individual patient, where the criteria takes into account the episode disease categories and severity of illness levels, where the criteria adjusts for the effect of interacting conditions in different episode disease categories.

2. The method of claim 1, step (e) further comprising defining severity of illness levels for each clinical risk group using episode disease categories or other factors.

3. The method of claim 1, step (d) further comprising defining the severity of illness rules for adjusting the severity of illness level for each episode disease category based on the nature and timing of treatment for each episode disease category.

4. The method of claim 3, wherein the severity of illness rules adjust the severity of illness level for each episode disease category based on the recency of other episode disease categories.

5. The method of claim 1, further comprising:
   a) providing a set of medical procedure codes;
   b) categorizing the medical procedure codes into episode procedure categories;
   wherein the severity of illness rules take account of the episode procedure categories in adjusting the severity of illness level for each episode disease category.

6. The method of claim 5, further comprising the step of creating episode disease categories that are indicated by episode procedure categories.

7. The method of claim 1, further comprising defining a set of selection criteria for selecting a primary chronic disease or identifying a lack of a primary chronic disease from the episode disease categories for each major disease category.

8. The method of claim 7, wherein step (e) comprises:
   a) defining criteria for a series of risk groups ranked in order of declining clinical significance;
   b) comparing the episode disease categories to the criteria for each risk group, and assigning the most severe clinical risk group for which the criteria are met.

9. The method of claim 1, further comprising defining criteria for an overall clinical risk group to a group of patients, where the criteria takes into account the episode disease categories and severity of illness levels.

10. The method of claim 1, further comprising applying the classification system to determining anticipated health care costs for an individual comprising:
    a) obtaining historical care data for an individual;
    b) determining the episode disease categories for the individual;
    c) adjusting the episode disease categories for the individual based on the nature and temporal relationships of the episode disease categories experienced by the individual.

11. The method of claim 10, wherein the adjusting step includes deleting episode disease categories when the temporal relationship between events implies that the disease indicated by an episode disease category has likely been eliminated by subsequent treatment.

12. The method of claim 10, further comprising the steps of:
    a) assigning a clinical risk group to the individual based on the adjusted episode disease categories experienced by the individual;
    b) identifying from adjusted episode disease categories the primary chronic disease in each major disease categories; and
    c) determining the clinical risk group based on the number and type of primary chronic diseases.

13. The method of claim 12, wherein the step of determining the clinical risk group is further based on the presence of catastrophic conditions.

14. The method of claim 12, further comprising the steps:
    a) determining the severity of illness level for each primary chronic disease experienced by the individual;
    b) setting a severity of illness level for each primary chronic disease based on the nature, temporal relationships and severity of illness levels of the episode disease categories experienced by the individual; and
    c) assigning an overall severity of illness for the individual based on the adjusted severity of illness levels for the primary chronic diseases experienced by the individual.

15. Computer storage media containing software which, when executed by a computer, will cause the computer to implement the following steps:
    (a) a computer system obtaining a set of medical disease codes;
    (b) categorizing the medical disease codes into major disease categories using the computer system;
    (c) categorizing the medical disease codes in each major disease category into episode disease categories based on severity of health care requirements using the computer system;
    (d) sub-dividing at least some of the episode disease categories using the computer system by severity of illness level by using severity of illness rules to take into account other episode disease categories or other information not related to a particular episode disease category being subdivided; and
    (e) defining criteria using the computer system for assigning an overall clinical risk group to an individual patient, where the criteria takes into account the episode disease categories and severity of illness levels, where the criteria adjusts for the effect of interacting conditions in different episode disease categories.

16. A method of creating a classification system for rating the nature and severity of health care requirements, including:
    (a) a computer system obtaining a set of medical disease codes;
    (b) categorizing the medical disease codes into major disease categories using the computer system;
    (c) categorizing the medical disease codes into episode disease categories in each major disease category based on severity of health care requirementsusing the computer system;
    (d) obtaining a set of medical procedure codes using the computer system;
    (e) categorizing the medical procedure codes into episode procedure categories using the computer system;
    (f) sub-dividing at least some of the episode disease categories using the computer system by severity of illness level by using severity of illness rules, wherein the severity of illness rules take into account temporal information including order of occurrence of the episode disease categories and episode procedure categories.

17. The method of claim 16 wherein the severity of illness rules take into account the recency of treatment for episode disease categories.

18. The method of claim 16, further comprising applying the classification system to determining anticipated health care costs for an individual comprising:
    a) obtaining historical care data for an individual;
    b) determining the episode disease categories for the individual;
    c) assigning severity levels to the episode disease categories for the individual based on the nature and temporal relationships of the episode disease categories experienced by the individual.

19. The method of claim 18, wherein the step of assigning severity levels includes deleting episode disease categories when the temporal relationship between events implies that the disease indicated by an episode disease category has likely been eliminated by subsequent treatment.

20. A method of creating a classification system for rating the nature and severity of health care requirements, including:
    (a) first, obtaining a set of medical disease codes using the computer system;
    (b) second, categorizing the medical disease codes into major disease categories using the computer system, wherein each major disease category corresponds to a single organ system, a malignancy or a multiple trauma;

(c) third, categorizing the medical disease codes in each major disease category into episode disease categories based on severity of health care requirements using the computer system; and (d) fourth, sub-dividing at least some of the episode disease categories using the computer system by severity of illness level by using severity of illness rules, thereby defining a set of severity of illness levels for each episode disease category.

21. The method of claim 20, wherein the severity of illness rules for adjusting the severity of illness level for each episode disease category are based on the nature of and temporal information about each episode disease category.

* * * * *

UNITED STATES PATENT AND TRADEMARK OFFICE
CERTIFICATE OF CORRECTION

| | |
|---|---|
| PATENT NO. | : 8,571,892 B2 |
| APPLICATION NO. | : 11/465901 |
| DATED | : October 29, 2013 |
| INVENTOR(S) | : Richard Averill |

It is certified that error appears in the above-identified patent and that said Letters Patent is hereby corrected as shown below:

Title Page
Item[56]; Page 2; References Cited; OTHER PUBLICATIONS;
Column 2; line 2; delete "htm" and insert -- html -- therefor.

In the Specification
Column 6
Line 12; delete "identified" and insert -- identified. -- therefor.
Line 15; delete "determined" and insert -- determined. -- therefor.
Line 19; delete "individual" and insert -- individual. -- therefor.
Line 21; delete "aggregation" and insert -- aggregation. -- therefor.

Column 7
Line 53; delete "death." and insert -- death -- therefor.

Column 9
Table 2; Rank 15; Type C; Line 17; delete "Ventrical" and insert -- Ventricle -- therefor.

Column 15
Table 4; Line 33; delete "Ventrical" and insert -- Ventricle -- therefor.

Column 17
Line 28-29; delete "ambulatory)" and insert -- ambulatory). -- therefor.

Column 21
Line 54; delete "for a an" and insert -- for an -- therefor.
Line 65; delete "focussing" and insert -- focusing -- therefor.

Signed and Sealed this
Fifteenth Day of April, 2014

Michelle K. Lee
*Deputy Director of the United States Patent and Trademark Office*

Column 22
Table 7; Line 34; delete "2 , 4, 6" and insert -- 2, 4, 6 -- therefor.

In the Claims
Column 28
Claim 16; Line 34; delete "requirementsusing" and insert -- requirements using -- therefor.